(12) United States Patent
Akerström et al.

(10) Patent No.: US 6,380,365 B1
(45) Date of Patent: Apr. 30, 2002

(54) TEMPERATURE DEPENDENT LIGAND FACILITATED PURIFICATION OF PROTEINS

(75) Inventors: Bo Akerström, Lund; Tommy Cedervall, Svedala, both of (SE)

(73) Assignee: Affitech AS, Oslo (NO)

( * ) Notice: Subject to any disclaimer, the term of this patent is extended or adjusted under 35 U.S.C. 154(b) by 0 days.

(21) Appl. No.: 09/305,852

(22) Filed: May 5, 1999

(30) Foreign Application Priority Data

Sep. 4, 1998 (GB) .............................................. 9819393
Nov. 6, 1998 (EP) .............................................. 98309128

(51) Int. Cl.[7] .............................. C07K 1/14; C07K 1/18; C07K 16/00
(52) U.S. Cl. ....................... 530/413; 530/412; 530/415; 530/417; 530/388.4
(58) Field of Search ............................ 435/69.1, 69.7, 435/320.1; 530/412, 413, 350, 415, 417, 388.4; 536/23.4

(56) References Cited

U.S. PATENT DOCUMENTS 5,670,631 A    9/1997   Bayerl et al. ................ 530/412

FOREIGN PATENT DOCUMENTS

EP    534 016 A1   3/1993
WO    WO 97/12988  4/1997

OTHER PUBLICATIONS

Baneyx et al. (1990) Enz. Microb. Technol. 12: 337–342.*
Jeppson et al. (1992) FEMS Microbiol. Lett. 92: 139–146.*
Baneyx et al., "Affinity immobilization of a genetically engineered bifunctional hybrid protein," *Enzyme Microb. Technology 12*: 337–342, May 1990.

Galaev et al., "Temperature–induced displacement of proteins from dye–affinity columns using an immobilized polymeric displacer," *Journal of Chromatography A 684*: 37–43, 1994.

Hollingshead et al., "Molecular Evolution of a Multigene Family in Group A Streptococci," *Mol. Biol. Evol. 11*(2): 208–219, 1994.

Jarrett and Taylor, "Transcription factor—green fluorescent protein chimeric fusion proteins and their use in studies of DNA affinity chromatography," *Journal of Chromatography A 803*: 131–139, 1998.

Jeppson et al., "Duplication of a DNA sequence homologous to genes for immunoglobulin receptors and M proteins in Streptococcus pyogenes," *FEMS Microbiology Letters 92*: 139–146, 1992.

Newman et al., "A computationally directed screen identifying interacting coiled coils from *Saccharomyces cerevisiae*," *Proceedings of the National Academy of Science USA 97*(24): 13203–13208, Nov. 21, 2000.

* cited by examiner

*Primary Examiner*—Karen Cochrane Carlson
*Assistant Examiner*—Rita Mitra
(74) *Attorney, Agent, or Firm*—Seed IP Law Group

(57) ABSTRACT

The invention concerns the use of a coiled coil protein which is capable of forming a homodimer which dissociates into monomers on change of temperature, in a method of isolating a ligand or desired protein from a sample. A method of isolating a ligand which binds to the coiled coil protein is described as well as methods of isolating a desired protein which is tagged with a coiled coil protein or a ligand which binds to a coiled coil protein, or is tagged with a coiled coil protein monomer.

23 Claims, 3 Drawing Sheets

TEMPERATURE DEPENDENT LIGAND FACILITATED PURIFICATION OF PROTEINS

CROSS-REFERENCES TO RELATED APPLICATION

This application claims priority from United Kingdom Application No. 9819393.1, filed Sep. 4, 1998, and European Patent Application No. 98309128.1, filed Nov. 6, 1998.

TECHNICAL FIELD

The invention relates to a method of chromatography and in particular to temperature related affinity chromatography.

BACKGROUND ART

Affinity chromatography is a widely used technique to purify proteins. This technique makes use of specific binding between two species for example two proteins. A sample containing a protein to be isolated is applied to a solid support having the other protein bound thereto. The specificity of binding between the two proteins leads to highly selective binding of the protein to be isolated to the solid support. A particular example is immunoaffinity chromatography where anti-ligand antibodies are bound to a solid support for purification of the ligand from a sample.

For affinity chromatography, it is desirable that the support bound protein has a strong and specific affinity for a desired protein to be purified. This strong and specific affinity is used to ensure that a high proportion of the desired protein in the sample is bound to the column with little or no binding of other impurities in the sample.

The desired protein must then be removed from the column. It is desirable that this protein will separate easily from the support bound protein so that the desired protein can be recovered in high yield and without affecting its integrity. However these conditions are often in conflict with the ability of the support-bound protein to bind the desired protein with high affinity and specificity. Thus in some circumstances the elution conditions required to remove the desired protein are unduly harsh and may lead to some denaturing or degradation of protein. Examples of current elution techniques are affinity elution with substrate or free ligand, change in pH or ionic strength, addition of a denaturing agent or changes in solvent polarity.

This technique can also be used to remove specific proteins from a sample e.g. immunoglobulins from plasma. Although in these circumstances there may be no further use for the immunoglobulin, it may still be desirable to release immunoglobulin from the column so that the column may be reused. As outlined above, the conditions required to elute the proteins from the column may be harsh, affecting not only immunoglobulin but also support bound protein.

DISCLOSURE OF THE INVENTION

This invention provides a method of affinity chromatography which makes use of a simple change in temperature to facilitate elution of a protein from a solid support thus avoiding harsh changes required in the prior art techniques. A coiled coil protein which is capable of forming a homodimer which dissociates into monomers on change of temperature is used in the method of isolating a ligand or desired protein from a sample.

In a first aspect the invention provides a method of isolating a ligand comprising providing a solid support having bound thereto a coiled coil protein which binds to said ligand and whose affinity for the ligand is temperature dependent, contacting a sample containing the ligand with the support at a temperature which promotes binding of the ligand to the protein and subsequently altering the temperature to promote dissociation of the ligand from the protein.

In a second aspect the invention provides a method of isolating a desired protein comprising tagging said protein with a coiled coil protein whose affinity for a ligand is temperature dependent or with a ligand which binds to the coiled coil protein; providing a solid support having bound thereto the other of the ligand or coiled coil protein; contacting a sample containing the tagged protein with the support at a temperature which promotes binding between the coiled coil protein and ligand; and subsequently altering the temperature to promote dissociation of the ligand from protein.

In a third aspect the invention provides a method of isolating a desired protein comprising tagging said protein with a coiled coil protein monomer; providing a solid support having bound thereto coiled coil protein monomer; contacting a sample containing the tagged protein with the support at a temperature which promotes binding between the monomer-tagged protein and support bound monomer to form a coiled coil; and subsequently altering the temperature to promote dissociation of the desired protein-monomer from the support bound monomer.

The temperature is generally raised to promote dissociation of binding.

DETAILED DESCRIPTION OF THE INVENTION

The technique can be used to purify a specific protein from a sample or to concentrate ligand for example where it is present in a very low concentration in a large volume. In the first aspect, it may also be used to remove undesired ligand from a sample, while allowing the column to be reused for further samples after elution of ligand from the column.

Figure 1:
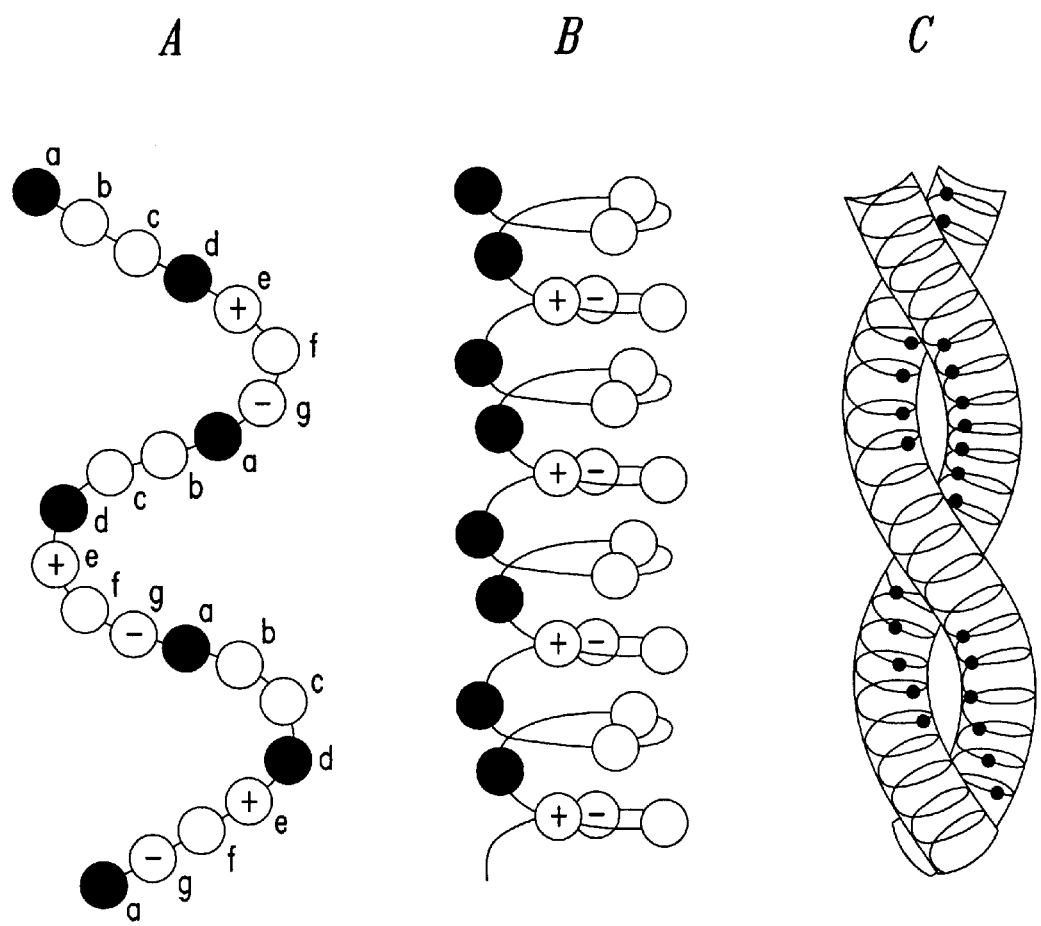
FIG. 1A–1C is a schematic view of the coiled coil proteins.

The invention makes use of the properties of certain coiled coil proteins which are temperature dependent. These proteins generally exist as dimeric coiled coil molecules comprising two α-helical peptides, which twist around each other. A schematic view of such proteins is shown in FIG. 1A–1C. The amino acid sequence of the peptides is arranged as seven residue repeats (FIG. 1A), called heptads, each heptad representing 2 turns of the α-helix (FIG. 1B). The residue positions within these heptads are designated a to g in FIG. 1A. The a and d positions are generally occupied by hyrdrophobic amino acids. The side-chains of these hydrophobic residues generally face the core of the coiled-coil molecule as shown in FIG. 1C and interact with the a and d positions of the other monomer. These hydrophobic interactions influence the stability of the coiled-coil molecules. In addition, interhelical ionic interactions can be formed by charged amino acids in positions e and g. Mammalian examples of coiled-coil proteins are myosin, tropomyosin, DNA-binding proteins and intermediary filaments.

Coiled-coil proteins are also found in the M proteins of Group A streptococci. Group A streptococci are common human pathogens that interact with the human host by binding one or more plasma proteins, such as fibrinogen, immunoglobulins, albumin and complement regulators. The binding of these plasma proteins is mediated by a family of related cell surface proteins called M proteins and M-like proteins, which constitute the M protein family. The M proteins share an overall structural organisation. They have unique N-terminal regions, conserved centrally located repeated regions and conserved C-terminal regions. The central repeats are of two distinct types, A or C, dividing the M proteins into class A and C proteins.

As mentioned above, the structure of some coiled coil proteins is temperature dependent, i.e. the proteins are coiled-coil dimers at low temperatures but unfolded monomers at 30–40° C. and higher temperatures. The present invention makes use of this change in structure so that the initial binding is carried out at temperatures which promote formation of coiled coils. Subsequently the temperature is altered so that the dimers dissociate.

In addition some of the coiled coil proteins will specifically bind to one or more entities such as for example plasma proteins. These entities are referred to herein as ligands. The binding affinity for these ligands may be temperature dependent.

In the case of some proteins, such as the M proteins, the coiled coil form is necessary for binding of specific ligands. Concomitantly with unfolding of the coiled coils, the affinity for the plasma protein ligands is lost. The temperature stability of the M proteins varies and some typical temperatures are set out in Table 1 together with the ligands and number of binding or unfolding domains.

TABLE 1

| Protein | Melting Point (° C.) | Ligands | Unfolding domains |
|---------|----------------------|---------|-------------------|
| Enn4 | 21 | IgA | 1 |
| M5 | 30 | Fibrinogen | 2 |
| Emm22 | 33 | IgA, IgG, C4BP | 2 |
| PAM | 28 | Plasminogen | 3 |
| Emm4 | 35 | IgA, IgG, C4BP | 2 |
| M1 | 37 | Fibrinogen, IgG, albumin factor H, kininogen | 3 |
| H | 29 | IgG, albumin, fibronectin, N-CAM, C4BP | 1 |
| Mrp4 | 74 | Fibrinogen, IgG | 3 |

(Emm4 and Emm22 were previously called Arp4 and Sir22 respectively).

For those coiled coil proteins which specifically bind one or more ligands, the effect of temperature can readily be monitored by looking at ligand binding. Alternatively labelled and unlabelled monomers can be used to observe the temperature change required to convert coiled coil dimers to dissociated monomers.

Generally the method will be carried out within a temperature range of about 0° C. to about 70° C. For isolation of human proteins the maximum temperature used is preferably about 40° C. Preferably the temperature change required to dissociate the coiled coils ($\Delta T$) is about 10 to 40° C., preferably about 15 to 20° C. $\Delta T$ needs to be sufficiently large so that it is practical to have clearly defined temperatures to promote dimerization and subsequent dissociation but not so large that (a) the temperature change is difficult to easily achieve in the laboratory or (b) the temperatures involved may disrupt the integrity of the ligand to be isolated. The actual temperature change may comprise a change from 5° C. to 20° C. or say 30° C. to 70° C., and preferably is from about 15% to 30° C. It may be desirable to cool the column and sample to be applied to the column if the contacting step is to be carried out below room temperature, or to warm the column and sample if the contacting step is carried out at raised temperature. The particular coiled-coil protein used for isolation of a particular ligand or desired protein can be selected by consideration of the temperature changes which can be borne by the ligand or desired protein.

The affinity chromatography method of the present invention can thus be used to purify a ligand such as plasma proteins by using, for example, a protein such as an M-protein which specifically binds the desired ligand, bound to a solid support. In this aspect of the invention, a coiled coil protein, such as M protein is first coupled to a solid support, for example, to a chromatography matrix forming the separation column. A sample containing ligand is then applied to the column and washed with a suitable buffer. The temperature is then raised for example by washing in buffer which has been heated to the desired temperature to elute ligand which has been extracted from the sample.

The sample is applied at a temperature at which the coiled coil protein exists in the dimerized state and thus has a higher affinity for the ligand. Thus the ligand is isolated from the sample by binding to the support-bound protein. As the temperature of the column is changed the coiled-coil dimers dissociate and thus the affinity for the ligand is reduced releasing the ligand from the column.

In alternative aspects, a desired protein which does not naturally bind to a coiled-coil protein may be purified. The desired protein is modified so that it will bind to the column-bound protein. The coiled-coil protein or its natural ligand is preferably bound to a solid support. The desired protein is then coupled to the natural ligand or the coiled-coil protein respectively to form a protein complex which binds to the solid support.

Alternatively, in a preferred aspect, the desired protein is modified to incorporate a coiled/coil protein monomer preferably attached via a linker peptide. The desired protein-monomer is maintained under conditions so that the monomers remain in undimerized form. The coiled-coil protein is bound to the support as monomer i.e. in uncoiled form. A sample containing the modified protein is applied to the column at a temperature which promotes dimer formation. The desired protein linked to protein monomer becomes bound to the column through dimerization of the protein monomers. After washing, the temperature is raised to elute the desired protein monomer. The desired protein can subsequently be dissociated from the monomer through cleavage to release the monomer. It is also possible to cleave the desired protein directly from the dimer on the column if desired.

This aspect may be used as the isolation step following expression of desired recombinant proteins. DNA encoding the coiled-coil monomer protein optionally together with a linker peptide, can be incorporated in frame adjacent DNA encoding the desired protein in an expression vector. Expression of the DNA produces fusion proteins comprising a coiled coil monomer and desired protein. The linker peptide may be used to provide a cleavage site to allow removal of the protein monomer from the desired protein. Alternatively the fusion protein may have a natural cleavage site to allow release of the protein monomer to leave the desired protein.

The temperature change can be carried out by applying heated buffer to the column. Alternatively a jacketed column may be used, the jacket comprising a heating element, or a heat conductive column. Alternatively the column may be incubated in a temperature controlled bath. A heating element may be moved through or down the column to release the ligand as it passes a particular portion of the column. For example, the column could be scanned to using e.g. a collimated beam of microwave radiation. It may be desirable to insulate the column to ensure that the temperature is constant, particularly for example when using warmed buffer to facilitate elution of the ligand i.e. to ensure that undesired variations in temperature are minimised.

Buffer applied to the column can also be used to change the pH, solvent polarity etc. and other parameters which reduce the affinity of the ligand for the bound protein. These changes can be used to enhance dissociation of the ligand from the bound protein but the dissociation is primarily effected by a change in the temperature. Where the method is being used to purify or isolate a desired protein, the use of other agents should be controlled to avoid contamination of the desired protein.

The coiled coil protein to be used is selected depending on the nature of the protein to be isolated. For example, if it is desirable to remove IgA from a sample, any temperature dependent proteins which bind IgA could be used such as, for example, Enn 4, Emm 22 or Emm 4. However if it is desirable to separate IgA from a sample which also contains IgG, Enn 4 would be more appropriate.

The coiled coil protein should also be selected to achieve the most desired temperature change.

For example, Emm 4, a class C protein, loses most of its coiled coil structure at temperatures below 37° C., whereas a class A protein, Mrp4, was found to be more temperature stable, i.e. its structure and plasma protein binding were retained at higher temperatures. Thus Emm4 may be more suitable for isolation of human proteins. Mrp4 has a much higher content of hydrophobic amino acids in positions a and d than the class C protein Emm4. In fact, the melting points (Tm) of several class C and class A proteins are strongly correlated to the content of hydrophobic side-chains in the predicted a and d positions of each protein. Thus the melting point of the coiled coil protein can be manipulated by mutation at these sites.

Table 1 above also demonstrates that coiled coil proteins may have several unfolding regions. The central regions, A- or C-repeats of the M proteins, behave as a single domain with a high coiled coil probability. The N-terminal regions, on the other hand, have a more complicated structure with regions of lower probability for coiled coil structure interrupted by non coiled coil regions. Thus, the N-terminal regions may contain several unfolding regions or domains. A few of the proteins, for example Enn4, have only one unfolding domain with a low Tm-value (Table 1). The proteins for use in accordance with the invention will comprise at least one coiled coil forming domain, and preferably comprise a single coiled coil domain. Enn4 is a particularly preferred protein.

The protein monomers and dimers for use in the present invention may be naturally occurring and isolated using standard techniques or may be produced, for example, by recombinant means. Suitable proteins generally form a coiled coil structure in a temperature dependent manner. Fragments of such proteins may also be used, such fragments incorporating at least one coiled coil domain.

Amino acid substitutions may be made, for example from 1, 2 or 3 to 10, 20 or 30 substitutions. The modified polypeptide generally forms the coiled coil structure. Conservative substitutions may be made, for example according to the following Table. Amino acids in the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

As outlined above, other substitutions may be made within the heptad structure to alter the temperature stability of the coiled coil.

The protein monomers or dimers can be bound to chromatographic matrix by standard techniques. Standard affinity chromatography matrices can be used such as Sepharose. The proteins may be coupled directly by CNBr-activated Sepharose. In an alternative and preferred aspect, coiled coil protein monomers or dimers are bound to a matrix such as pyridyl dithio Sepharose through a C- or N-terminal cys-residue or by other conventional coupling methods. Cys can be introduced for example by recombinant techniques. Coupling through a Cys-residue may reduce any interference in the unfolding of the protein which can occur with CNBr-activated Sepharose where the protein may be covalently linked to the column at several sites along its length.

The undimerized form of protein for application to the column or for the desired protein-monomers can be ensured through selection of appropriate temperature, concentration or pH. The monomer may be applied to the support at a concentration so that the monomers are linked to the support at a distance from one another preventing the protein forming homodimers. The monomer may be applied to the column in the presence of a chaotropic or denaturing agent which is subsequently washed off once the monomer is bound to the support. Preferably the denaturing agent is free of primary amino groups to avoid reacting with the activated matrix.

The solid support may be in the form of beads. In this embodiment, monomers or dimers may be coupled to beads. Once the binding of ligand has occurred, the beads are, e.g. centrifuged to isolate the beads with bound ligand. The ligand is then eluted as before.

The invention also relates to polynucleotides encoding the derived protein, linked to a coiled-coil protein monomer. A peptide linker sequence may be incorporated and preferably will comprise up to 10 amino acids in length and may comprise a unique cleavable site, such a site not being found in either the desired protein or the monomer. Examples of such sequences are flexible linkers such as RECER sequences, and the hinge region of immunoglobulin G or oligo-glycine, oligo-serine, oligo-Gly-Ser. Proline may be incorporated to prevent the linker from becoming rigidified into a helical structure like that of the coiled coil.

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Preferably, a polynucleotide of the invention in a vector is operably linked to a control sequence which is capable of providing for the expression of the coding sequence by the host cell, i.e. the vector is an expression vector. Such expression vectors can be used to express the desired protein/monomer for purification in the method of the invention.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Such vectors may be transformed into a suitable host cell as described above to provide for expression of a polypepride or polypeptide fragment of the invention. Thus, in a further aspect the invention provides a process for preparing polypeptide or polypeptide fragment according to the invention, which process comprises cultivating a host cell transformed or transfected with an expression vector as described above under conditions to provide for expression of the polypeptide or fragment, and recovering the expressed polypeptide or fragment.

The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell.

A further embodiment of the invention provides host cells transformed or transfected with the vectors for the replication and expression of polynucleotides of the invention. The cells will be chosen to be compatible with the said vector and may for example be bacterial, yeast, insect or mammalian.

Promoters and other expression regulation signals may be selected to be compatible with the host cell for which the expression vector is designed. For example, yeast promoters include *S. cerevisiae* GAL4 and ADH promoters, *S. pombe* nmt1 and adh promoters. Mammalian promoters include the metallothionein promoter which can be induced in response to heavy metals such as cadmium. For use in insect cells, strong baculovirus promoters such as the polyhedrin promoter are preferred. For expression in mammalian cells, strong viral promoters such as the SV40 large T antigen promoter, a CMV promoter or an adenovirus promoter may also be used. All these promoters are readily available in the art.

Expression vectors of the invention may be introduced into host cells using conventional techniques including calcium phosphate precipitation, DEAE-dextran transfection, or electroporation.

The expression vector may contain a selectable marker and/or such a selectable marker may be co-transfected with the expression vector and stable transfected cells may be selected.

Suitable cells include cells in which the abovementioned vectors may be expressed. These include microbial cells such as bacteria such as *E. coli*, mammalian cells such as CHO cells, COS7 cells or Hela cells, insect cells or yeast such as Saccharomyces. Baculovirus or vaccinia expression systems may be used.

Cell culture will take place under standard conditions. Commercially available cultural media for cell culture are widely available and can be used in accordance with manufacturers instructions.

The following Example illustrate the invention.

EXAMPLE

Figure 2:
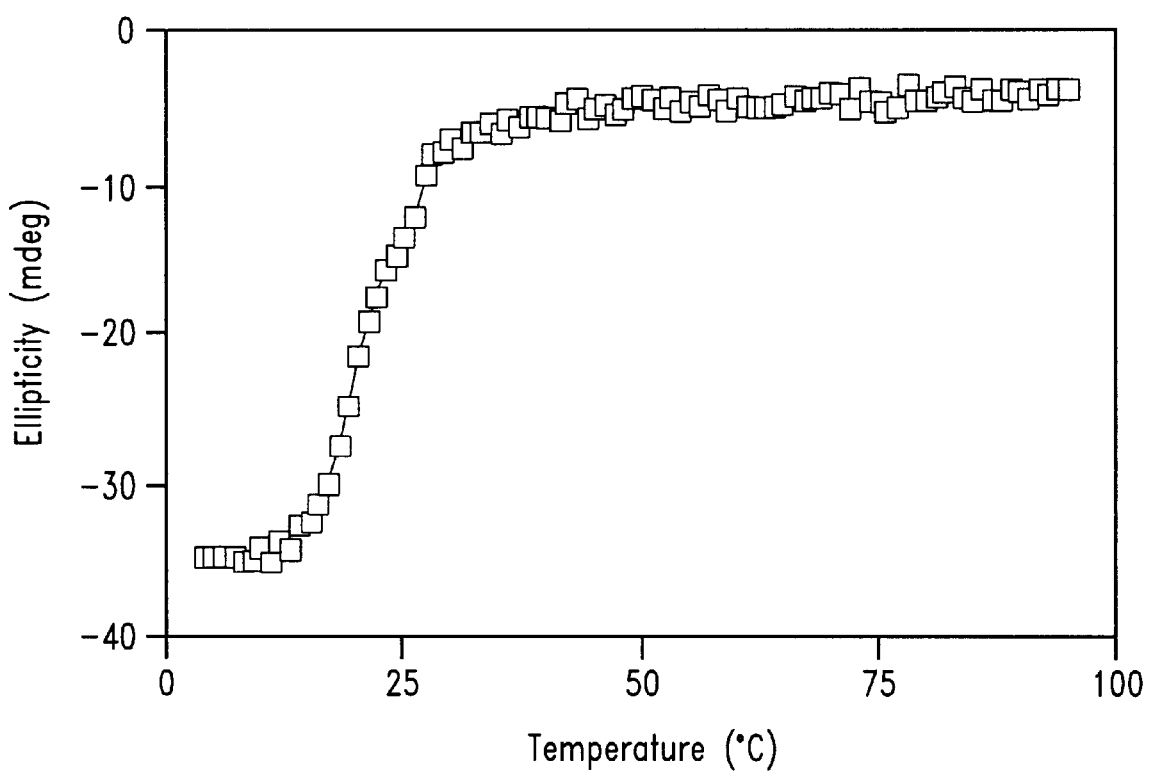
FIG. 2 shows the unfolding of a coiled coil protein Enn4 as a function of temperature.

The thermal stability of Enn4 was investigated and the results suggest that Enn4 is especially preferred among the M proteins. An unfolding diagram is shown in FIG. 2. Two properties are especially favorable. First, as seen in the figure, Enn4 has folded structure at 13° C. and is completely unfolded at 28° C. This suggests that the binding is maximal at 13° C. or lower and complete elution can be obtained at 28° C. or higher temperatures.

Secondly, Enn4 has only one unfolding domain, which means that it will be possible to "melt" the protein completely by a relatively limited elevation of the temperature (by approximately 15° C.).

Figure 3:
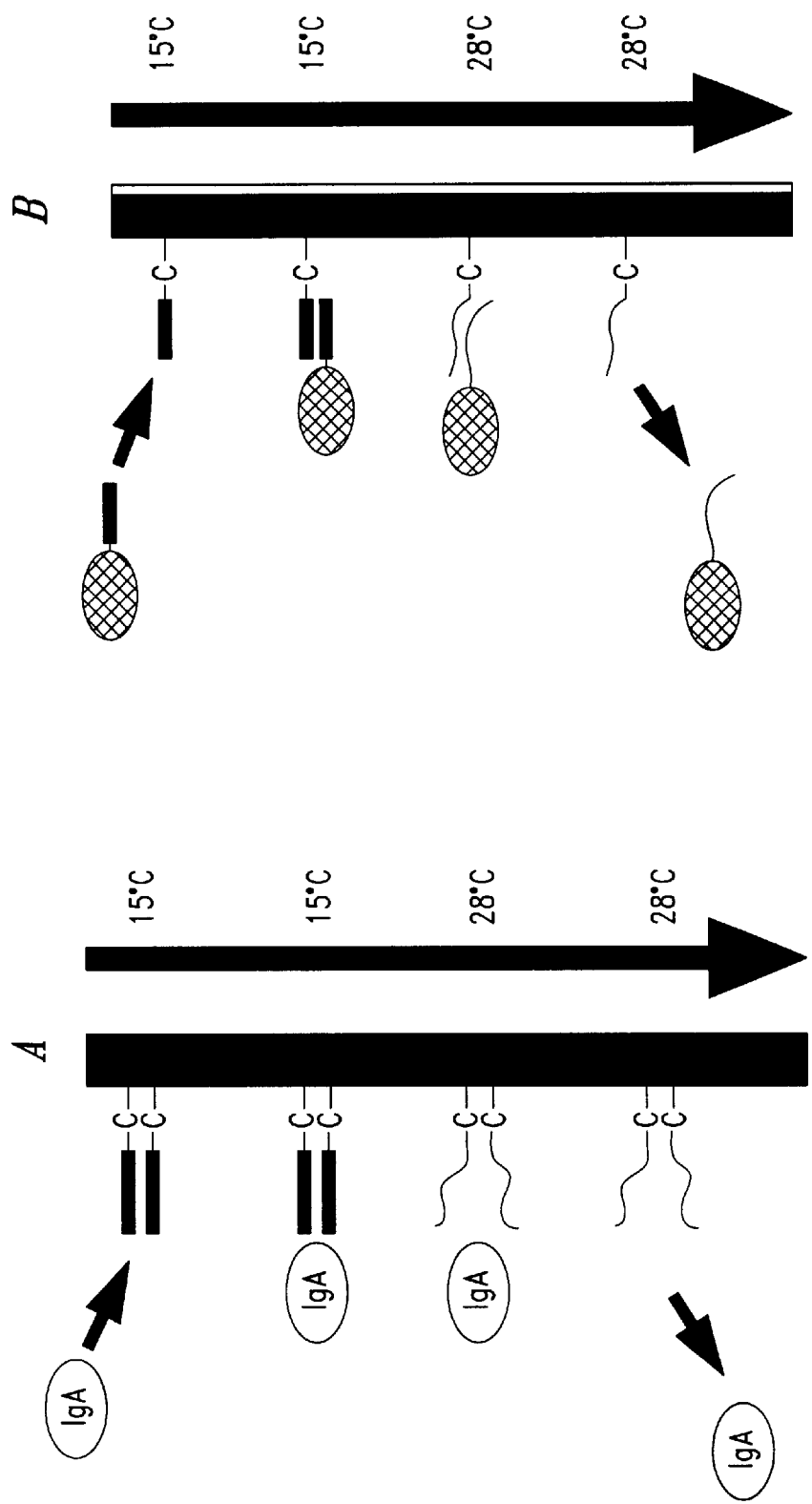
FIG. 3 is a schematic view of two purification techniques of the present invention.

FIG. 3 shows the principles involved in two of the purification systems of the invention. This figure shows an affinity chromatography system for (a) purification of IgA by coupling Enn4 to a chromatography matrix in a manner that permits full coiled-coil structure and complete and reversible denaturation of the insolubilized M protein; and (b) purification of any fusion protein comprising three parts: Enn4, a linker peptide and another protein, by interaction with insolubilized Enn4.

In system (a), Enn4 was immobilized in its coiled-coil state (bars) to a matrix (Sepharose). Human plasma was applied at 15° C. and IgA bound to Enn4. The column was rinsed with a salt solution at 15° C. The salt solution was then warmed to 28° C., which denatured Enn4 (thin lines), and IgA eluted from the column. The column can be reconstituted, i.e. Enn4 refolded by lowering the temperature to 15° C. again.

In example b) Enn4 was immobilized in its denatured state and thus could not form coiled-coil dimers on the matrix. A fusion protein, comprising any protein (dotted) linked to Enn4 through genetic recombination, was applied to the column at 15° C. Enn4, in the fusion protein bound strongly to the matrix by forming a coiled-coil dimer. The column was rinsed at 15° C. The salt solution was then warmed to 28° C., Enn4 denatured and the fusion protein eluted from the column.

The coupling of Enn4 is optimized by varying the concentration of Enn4, the ratio Enn4:gel volume and other parameters until a column is obtained in which Enn4 can be completely and reversibly uncoiled by heating. The columns can readily be tested by binding of human serum-IgA, which has been shown to have high affinity for Enn4. The capacity and reversibility of the Enn4-IgA interaction can be analyzed. Elution of the bound IgA is tested at various temperatures, simply by adding prewarmed buffer solutions. The optimized Enn4-column is then used for large scale (0.1–1 g) purification of IgA from human serum, and the purification schedule characterized and optimized. Ideally, IgA is purified by applying human serum to an Enn4-column, rinsing with a mild, physiological buffer at 15° C. and eluting the pure protein by warming the same buffer to 28° C.

As mentioned above, the coiled-coil structure involves a formation of homodimers of the M proteins. This property was exploited in the second application (b) of Enn4. When Enn4 is heated above 28° C. the protein dissociates into unfolded monomers. When the molecule is immobilized on the matrix via the C-terminal cys-residue at this temperature at an appropriate dilution, Enn4 monomers are covalently linked at a distance from each other, preventing the protein from forming homodimers when the temperature is lowered again to room-temperature.

The Enn4-tag is preferably prepared by expressing recombinant DNA comprising DNA encoding Enn4, a linker and the desired protein. The nucleotide sequence of Enn4 has been submitted to the EMBL/Genebank/DDBJ Nucleotide Sequence Databases under accession No Z11602. Enn4 tagged molecules added to the column are able to interact with the immobilized Enn4 by coiled-coil dimerization, and eluted again by warming the elution buffer. By this principle, it is possible to purify fusion proteins carrying an Enn4-tag.

The present invention has been detailed both by direct description and by example. Equivalents and modifications of the present invention will be apparent to those skilled in the art and are encompassed within the scope of the invention.

What is claimed is:

1. A method of isolating a ligand comprising the steps of:
   a. providing a solid support having bound thereto a coiled coil protein, which binds to said ligand and whose affinity for the ligand is temperature dependent;
   b. contacting a sample containing the ligand with the support at a temperature which promotes binding of the ligand to the protein;
   c. altering the temperature to promote dissociation of the ligand from the protein; and
   d. collecting said ligand.

2. The method of claim 1 wherein the change of temperature of the column is in the range of about 10 to 40° C.

3. The method of claim 1 wherein the step of altering the temperature of the column comprises passing heated buffer through the column.

4. The method of claim 1 wherein the coiled coil protein is an M protein of a group A Streptococcus.

5. The method of claim 4 wherein the coiled coil protein is Enn4.

6. A method of isolating a desired protein comprising the steps of:
   a. tagging said protein with a coiled coil protein monomer;
   b. providing a solid support having bound thereto coiled coil protein monomer;
   c. contacting a sample containing the tagged protein with the support at a temperature which promotes binding between the monomer tagged protein and support-bound monomer;
   d. altering the temperature to promote dissociation of the desired protein-monomer from the support bound monomer; and
   e. collecting the desired protein-monomer.

7. The method of claim 2 further comprising the step of removing the coiled coil protein monomer from the desired protein.

8. The method of claim 6 wherein the change in temperature of the column is in the range of about 10 to 40° C.

9. The method of claim 6 wherein the step of altering the temperature of the column comprises passing heated buffer through the column.

10. The method of claim 6 wherein the coiled coil protein is an M protein of a group A Streptococcus.

11. The method of claim 10 wherein the coiled coil protein is Enn4.

12. A method of isolating a desired protein comprising the steps of:
    (a) tagging said desired protein with a coiled coil protein whose affinity for a ligand is temperature dependent;
    (b) providing a solid support having bound thereto said ligand;
    (c) contacting a sample containing the tagged protein with the support at a temperature which promotes binding between the coiled coil protein and ligand;
    (d) altering the temperature to promote dissociation of the protein from the ligand; and
    (e) collecting said tagged protein.

13. The method of claim 12 further comprising the step of removing the tag from the desired protein.

14. The method of claim 12 wherein the change of the temperature of the column is in the range of about 10 to 40° C.

15. The method of claim 12 wherein the step of altering the temperature of the column comprises passing heated buffer through the column.

16. The method of claim 12 wherein the coiled coil protein is an M protein of a group A Streptococcus.

17. The method of claim 16 wherein the coiled coil protein is Enn4.

18. A method of isolating a desired protein comprising the steps of:
    (a) tagging said desired protein with a ligand which binds to a coiled coil protein whose affinity for a ligand is temperature dependent;
    (b) providing a solid support having bound thereto said coiled coil protein;
    (c) contacting a sample containing the tagged protein with the support at a temperature which promotes binding between the coiled coil protein and ligand;
    (d) altering the temperature to promote dissociation of the tagged protein from the coiled coil protein; and
    (e) collecting said tagged protein.

19. The method of claim 18 further comprising the step of removing the tag from the desired protein.

20. The method of claim 18 wherein the change of the temperature of the column is in the range of about 10 to 40° C.

21. The method of claim 18 wherein the step of altering the temperature of the column comprises passing heated buffer through the column.

22. The method of claim 18 wherein the coiled coil protein is an M protein of a group A Streptococcus.

23. The method of claim 22 wherein the coiled coil protein is Enn4.

* * * * *

UNITED STATES PATENT AND TRADEMARK OFFICE
CERTIFICATE OF CORRECTION

PATENT NO. : 6,380,365 B1
DATED : April 30, 2002
INVENTOR(S) : Bo Akerström et al.

It is certified that error appears in the above-identified patent and that said Letters Patent is hereby corrected as shown below:

<u>Column 9,</u>
Line 59, "The method of claim 2" should be corrected to read -- The method of claim 6 --.

Signed and Sealed this

Twenty-fourth Day of September, 2002

Attest:

Attesting Officer

JAMES E. ROGAN
*Director of the United States Patent and Trademark Office*